(12) United States Patent
Shelar et al.

(10) Patent No.: US 8,623,849 B2
(45) Date of Patent: Jan. 7, 2014

(54) MEDICINAL APPLICATIONS OF BENZOIC ACID HYDRAZONES SYNTHESIZED ON THE BASIS OF STEROIDAL TIGOGENIN

(75) Inventors: Ashok Ranganath Shelar, Kolhapur (IN); Maia Merlani, Tbilisi (GE); Milind Shelar, Kolhapur (IN); Lela Amiranashvili, Tbilisi (GE); Balkrishna Shelar, Kolhapur (IN)

(73) Assignee: Ashok Ranganath Shelar, Kolhapur (IN)

( * ) Notice: Subject to any disclaimer, the term of this patent is extended or adjusted under 35 U.S.C. 154(b) by 291 days.

(21) Appl. No.: 12/736,816

(22) PCT Filed: Mar. 3, 2009

(86) PCT No.: PCT/IN2009/000139
§ 371 (c)(1),
(2), (4) Date: Mar. 22, 2011

(87) PCT Pub. No.: WO2009/144738
PCT Pub. Date: Dec. 3, 2009

(65) Prior Publication Data
US 2011/0178317 A1    Jul. 21, 2011

(51) Int. Cl.
*A61K 31/565* (2006.01)
*C07J 41/00* (2006.01)

(52) U.S. Cl.
USPC .......................... 514/169; 514/182; 552/518

(58) Field of Classification Search
USPC .................................. 552/518; 514/169, 182
See application file for complete search history.

(56) References Cited

FOREIGN PATENT DOCUMENTS

WO        WO 01/08677    *    2/2001

OTHER PUBLICATIONS

Volovel'skii, "Synthesis of derivatives of androstane series. IX. Tetrahydrazones of 2,16-dihydroxymethyleneandrostane-3,17-dione and 2,16-bis(ydroxymethylene)-4-androstene-3,17-dione." Zhurnal Obshchei Khimii, vol. 36(2), pp. 239-242, 1966.*
Volovel'skii et al., "Potential antitumor compounds. I. Hydrazones and bis(chloroethyl)hydrazone derivatives of cholestan-3-one." Zhurnal Obshchei Khimii, vol. 37(7), pp. 1571-1579, 1967.*

* cited by examiner

*Primary Examiner* — Barbara P Badio
(74) *Attorney, Agent, or Firm* — Ladas & Parry LLP

(57) ABSTRACT

Novel benzoic acid hydrazones of 5α-androstan-3,17-dione have been prepared on the basis of steroidal tigogenin of the plant *Yucca gloriosa*. The hydrazones of the General Formula (I), General Formula (II) and General Formula (III) as shown in the accompanying FIGURE of the drawing are synthesized. The hydrazones have shown promising anti-T.B., anti-cancer and anti-HIV activity revealing immense potential as more efficacious, less toxic drugs with fewer undesirable side effects. They could also prove valuable in correcting hormonal abnormalities that cause severe health problems.

3 Claims, 1 Drawing Sheet

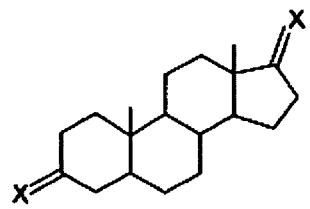
General Formula ( I )
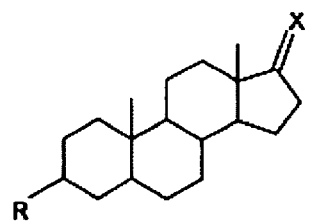
General Formula ( II )
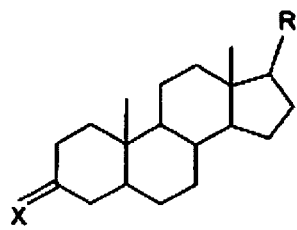
General Formula ( III )
Where,
R= OH, OCH3, F, CH3 etc
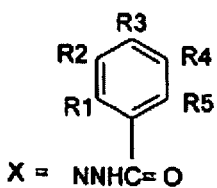
X = NNHC= O
and  R1=R2=R3=R4=R5= NO2,NH2,F,Cl,Br,OCH3,CH3,H etc.

MEDICINAL APPLICATIONS OF BENZOIC ACID HYDRAZONES SYNTHESIZED ON THE BASIS OF STEROIDAL TIGOGENIN

FIELD OF INVENTION

In recent years chemical research in the steroid field has gone hand in hand with chemical investigation to develop a wide variety of steroid derivatives, not found in nature, which have specific physiological action and medical application. Small variations in the structure of steroid molecules frequently results in wide variations in the physiological activity and help in search of new drugs with enhanced potency, broader applicability, lower toxicity and fewer undesirable side effects. Steroid therapy is becoming increasingly important in modern medicine, and runs the gamut from preventing abortion to arresting certain cancers, from controlling pregnancy to treating arthritis, and from correcting hormonal abnormality to treating dermatitis. Dexamethasone, a fluorine containing steroid, is used in treating inflammation, the acetylinic derivative of 19-norethisterone exerts control over the menstrual cycle and used as oral contraceptive, and the triketone prednisone finds general application in the field of cortisone therapy.

Steroids include a wide variety of natural products containing the cyclo pentano perhydrophenanthrene ring system present in cholesterol.

Tuberculosis

The significant increase in the incidence and morbidity from tuberculosis since the start of the 1990's prompted the World Health Organization to regard the disease as a worldwide danger. One of the factors leading to the increased incidence is the development of resistance in the *Mycobacterium tuberculosis*. One in every 20 new cases of TB worldwide is now resistant to two or more drugs. Half a million new cases of MDR-TB and 40,000 new cases of XDR-TB are emerging each year across the globe, 110,000 people with MDR-TB die every year from the disease as per the data collected between 2002-2006 on TB patients in 81 countries, Therefore the search for new effective anti-tuberculosis compounds has become urgent.

Cancer

Cancer chemotherapy uses compounds that can differentiate to some degree between normal tissue cells and cancer cells. The decision to use a certain anti-neoplastic drug depends on type and location of tumor. Therefore it is imperative to keep searching for new compounds.

HIV

HIV infection in humans is now a pandemic. As of January 2006, the joint United Nations Programme on HIV/AIDS (UNAIDS) and the World Health Organization (WHO) estimate that AIDS has killed more than 25 million people since it was first recognized on Dec. 1, 1981 making it one of the most destructive pandemics in recorded history in 2005 alone, AIDS claimed an estimated 2.4-3.3 million lives. About 0.6% of worlds living population is infected with HIV. Antiretroviral reduces both mortality and morbidity of HIV infection, but access to anti-retroviral medication is not available in all countries.

BACKGROUND OF THE INVENTION

A number of steroidal compounds with NH2, N-alkyl, N-alkyloxy, N,N-dialkyl etc. substituents in the C-17 position that exhibit a broad spectrum of biological activity have been synthesized based on tigogenin. Synthesis of 5α-androstan-3β,17-β-diols were reported as potential anticancer compounds. Novel steroidal isonicotin hydrazones and thiosemicarbazones were reported as potential anti T.B. agents.

Some Copyright Compounds
(A) Formula: C20 H31 N3 S
CA Index Name: Androst-2-en-17-one (aminothioxomethyl) hydrazone
Registry No. 487039-91-8
Copyright 2007 American Chemical Society

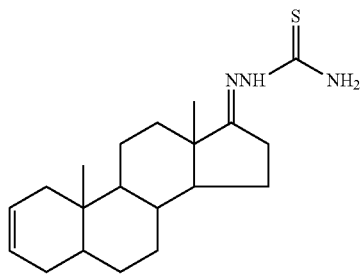

(B) Formula: C26H36 O3 S
CA Index Name: Androst-2-en-17-ol, 4-methylbenzenesulphonate
Registry No. 913816-27-0
Copyright 2007 American Chemical Society
(C) Formula: C1911300
CA Index Name: Androst-2-en-17-ol
Registry No. 6699-64-5
Copyright 2007 ACS
(C) Formula: C19 H33 N O
CA Index Name: 5β-androstane-3-o1,17-amino-,
Registry No. 32911-76-5
Copyright 2007 ACS

REFERENCES

1. Camoutis C., Trafalis D., Int. New Drugs 2003 21 47
2. Amiranashvili L., Merlani M., Menshova N., Suvorov N., Bull. Georg. Acad. Sci. 1998 158 (2) 2
3. Merlani M. I., Kemertelidze E. P., Papadopoulos K:, Menshova N. I., Bioorg Khim. 2004 30 552 [Engl. transl. Russ. J. Bioorg. Chem. 2004 30 000].

BRIEF DESCRIPTION OF THE DRAWINGS

FIG. 1 illustrates general Formulae (I), (II), and (III), of the present invention.

DETAILED DESCRIPTION OF THE INVENTION

Steroidal sapogenin-tigogenin was proposed as starting material for synthesizing 5a-series. Tigogenin is isolated from the plant *Yucca gloriosa*, which is cultivated in Georgia [1]. We developed a synthetic scheme for acetate eoiandrosterone based on tigogenin (1) that involves conversion of 1 to pregnenolone acetate (2), of 2 to epiandrosterone acetate. For conversion of 1 to 2, we chose oxidative dehydration using TiC14 as catalyst. The yield of 2 from 1 was 69.5% [2]. Compound 2 was converted to epiandrosterone acetate using the Schmidt-Thome method [3], according to which pregnenolone acetate oxime (3) underwent Beckmann rearrangement by POCl$_3$ in pyridine. Acid hydrolysis of intermediate 17-acetylamino derivative 4 gave epiandrosterone acetate (5) in 65% yield [4].

3β-Acetoxy-5α-pregn-16-en-20-one (2). A mixture of 1 (50 g, 120.0 mmol), $(CH_3CO)_2O$ (150 mL), and $C_5H_5N$ (10 mL) was boiled for 1 h, cooled to 100° C., stirred, treated with $TiCl_4$ (2.5 g, 13.16 mmol) in $(CH_3CO)_2O$ (2.5 mL), boiled an additional 2 h, cooled to 40° C., treated gradually with $CH_3COONa$ (10 g) dissolved in water (25 mL), stirred 20 min, cooled to room temperature, poured into $CH_3COCH_3$ (220 mL) and $CH_3COOH$ (220 mL), oxidized by addition of $CrO_3$ (15 g) in water (7.5 mL) at 15-18° C., stirred an additional hour, treated with isopropanol (7.5 mL), gradually heated to distill off acetone and reach a temperature of 115-117° C., boiled for 1.5 h, cooled to room temperature, and treated with water (425 mL). The resulting precipitate was filtered off, washed with water, and recrystallized from methanol:acetone (3:1) to afford 2 (29 g, 69.5%), mp 158-162° C., lit. mp 158-162° C. [2].

5α-Pregn-16-en-3β-o1-20-one Acetate Oxime (3). A mixture of 2 (2.5 g, 6.97 mmol), $NH_2OH.HCl$ (0.55 g, 7.91 mmol), and dry $C_5H_5N$ (12 mL) was heated at 65-68° C. for 2 h, cooled to room temperature, treated with water (45 mL), and stirred for 30 min. The resulting precipitate was filtered off and washed with water to afford 3 (2.5 g, 98.07%), mp 196-198° C., lit. mp 195.5-98.5° C. [4].

3β-Acetoxy-5α-androstan-17-one (5). A mixture of 3 (1 g, 2.67 mmol), dry $C_5H_5N$ (3.2 mL), and dry $CH_3COCH_3$ (3.2 mL) at 18-20° C. was treated with $POCl_3$ (1.2 mL), stirred for 30 min, cooled to −5° C., treated with dilute HCl (1:1 with water, 28 mL), stirred for 30 min, and treated with water until neutral. The resulting precipitate was filtered off and washed with water to afford crude product (0.83 g) that was chromatographed over a column of silica gel (L 100-160) with elution by low-boiling petroleum ether:ether (20:1) to afford 5 (0.58 g, 65%), mp 111-113° C., lit. mp 111-13° C. [4].

3β-hydroxy-5α-androstan-17-one (6). A mixture of 5 (1 g, 3.00 mmol), NaOH 0.12 g (3.44 mmol) in methanol was refluxed for 10 min, cooled to room temperature and treated with water. The resulting precipitate was filtered off and washed with water to afford crude product 6 (0.82 g, 95%).

5α-androstan-3,17-dione (7). To the mixture of 6 (5 g, 17.2 mmol) and 75 ml acetone at room temperature 1.5 ml of Jones reagent ($CrO_3$, $H_2SO_4$, $H_2O$) was added by drops. After the reaction was completed, NaOH was added, liquid phase was separated and then 90 ml water was added. The resulting precipitate was filtered off to afford product 7 (4.72 g, 94%). M.p. 134-137° C.

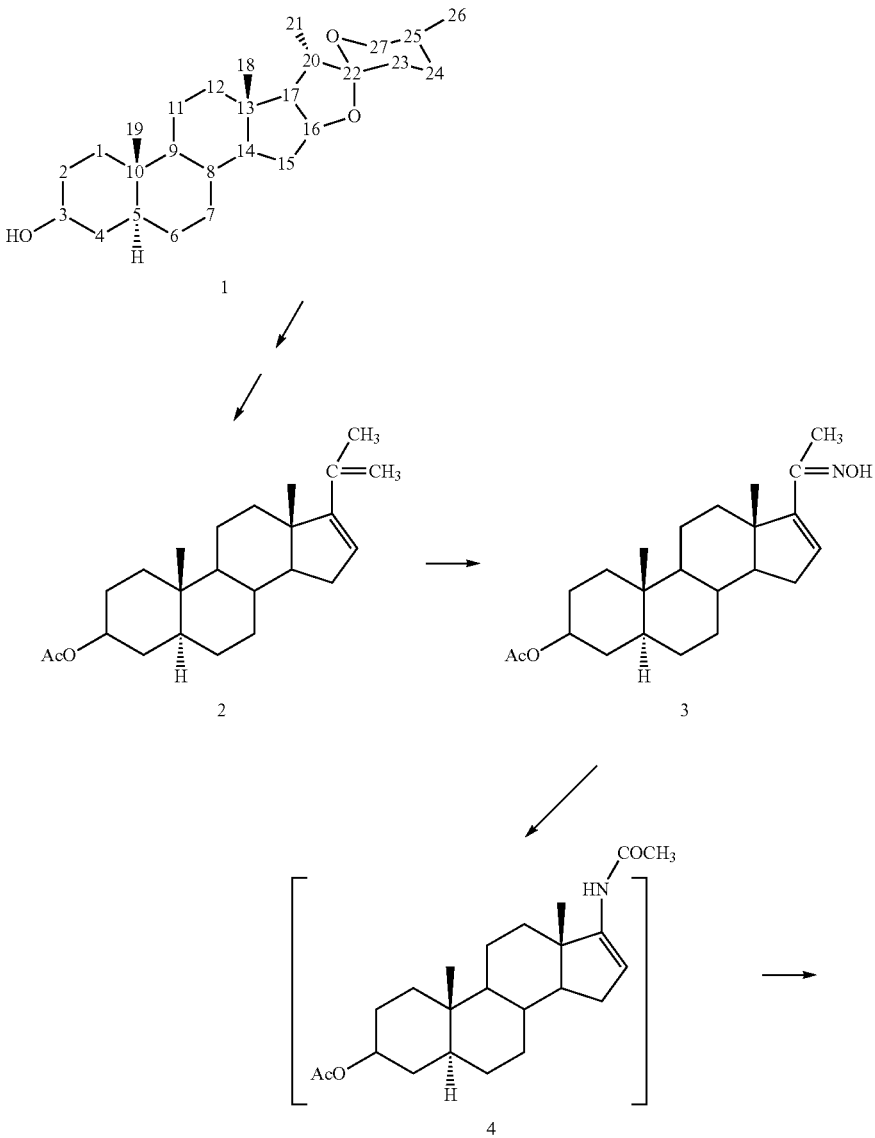

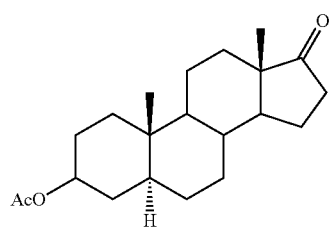

5

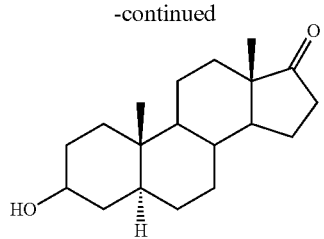

6

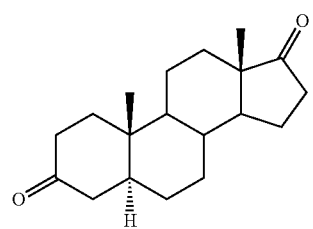

7

Preparation of Novel Benzoic Acid Hydrazones

Bis-{3-brombenzoic acid [(5α)-androstan-3,17-ylidene]}-hydrazide Bis-m-brombenzoic acid hydrazone of 5a-androstane-3,17-dione. A mixture of 5a-androstane-3,17-dione (1 g, 3.46 mmol), m-brombenzoic acid hydrazide (1.49 g, 6.93 mmol) and acetic acid (1 ml) in ethanol (10 ml) was refluxed for 2 h and cooled to room temperature. The precipitated solid was filtered, washed with water, and recrystallized from ethanol to give desired hydrazone; yield 93%; mp 165-167° C. Structural Formula (I).

IR (KBr, cm$^{-1}$): 3475 (NH), 1700 (NHC=O), 1643 (C=N), 1550 (aromatic ring), $^1$H NMR (500 MHz, CDCl$_3$), δ: 0.83 (3H, s, C18-H3), 0.90 (3H, s, 19-CH3), 7.64-7.89 (10H, in, aromatic protons), 8.17 (1H, br s, NH), 8.31 (1H, br s, NH) $^{13}$C NMR (500 MHz, CDCl$_3$), δ: 11.11 (CH$_3$), 16.95 (CH$_3$), 122.91-150.11 (aromatic ring) 161.21 (C=N), 162.22 (C=N), 171.22 (C=O).

Bis nitrobenzoic acid [((5a)-androstan-3,17-ylidene])-hydrazide

Bis-m-nitrobenzoic acid hydrazone of 5a-androstane-3,17-dione. A mixture of 5a-androstane-3,17-dione (1 g, 3.46 mmol), m-nitrobenzoic acid hydrazide (1.25 g, 6.93 mmol) and acetic acid (1 ml) in ethanol (10 ml) was refluxed for 2 h and cooled to room temperature. The precipitated solid was filtered, washed with water, and recrystallized from ethanol to give desired hydrazone; yield 90%; mp 202. 205° C. Structural Formula (II)

IR (KBr, cm$^{-1}$): 3484 (NH), 1700 (NHC=O), 1639 (C=N), 1528 (aromatic ring), $^1$H NMR (500 MHz, CDCl3), δ: 0.83 (3H, s, C18-H3), 0.90 (3H, s, 19-CH3), 7.64-7.89 (10H, in, aromatic protons), 8.17 (1H, br s, NH), 8.31 (1H, br s, NH) $^{13}$C NMR (500 MHz, CDCl$_3$), δ: 11.23 (CH$_3$), 17.26 CH$_3$), 122.91-147.11 (aromatic ring), 161.21 (C=N), 162.22 (C=N), 176.22 (C=O).

3-Nitrobenzoic acid [(3α, 5α)-3-hydroxyandrostan-17-ylidenel-hydrazide m-nitrobenzoic acid hydrazone of 3α-hydroxy-5α-androstan-17-one. A mixture of 3α-hydroxy-5α-androstan-17-one (100 mg, 0.34 mmol), m-nitrobenzoic acid hydrazide (0.74 mg, 0.41 mmol) and acetic acid (1 ml) in ethanol (5 ml) was refluxed for 12 h and cooled to room temperature. The precipitated solid was filtered, washed, washed with water, and recrystallized from ethanol to give desired hydrazone; yield 85%; mp 305. –07° C.

REFERENCES

1. E. P. Kemertelidze and T. A. Pkheidze, *Khim-Farm*. Zh., 6, 44 (1972).
2. L. K. Kavtaradze, R. I. Dabrundashvili, N. I. Men'shova, N. A. Korzinkina, and E. P. Kemertelidze, *Soobshch. Akad. Nauk Gruz*. SSR, 132, No. 3, 537 (1988).
3. J. Schmidt-Thome, Chem. *Ber.*, 88, 895 (1955).
4. N. I. Men'shova, N. A. Korzinkina, E. P. Kemertelidze, N. Sh. Nadaraia, M. G. Davitishvili, L. I. Lishcheta, and V. S. Grosheva, *Sb. Nauchn. Tr. VNIKhFi im. S. Ordzhonikidze*, 10, 83 (1982).

What is claimed is:

1. A bis-[m-bromobenzoic acid hydrazone] of 5α-androstane-3,17-dione.
2. A bis-[m-nitrobenzoic acid hydrazone] of 5α-androstane-3,17-dione.
3. A m-nitrobenzoic acid hydrazone of 3α-hydroxy-5α-androstane-17-one.

* * * * *